United States Patent [19]

Krauter et al.

[11] Patent Number: 4,875,468
[45] Date of Patent: Oct. 24, 1989

[54] ELASTOMER-EPTFE BIOPSY CHANNEL

[75] Inventors: Allan I. Krauter, Syracuse; Robert L. Vivenzio, Auburn, both of N.Y.

[73] Assignee: Welch Allyn, Inc., Skaneateles Falls, N.Y.

[21] Appl. No.: 289,324

[22] Filed: Dec. 23, 1988

[51] Int. Cl.⁴ .............................................. A61B 1/00
[52] U.S. Cl. ...................................... 128/3; 128/348.1; 128/DIG. 14; 604/280; 604/283
[58] Field of Search ...................... 128/3, 4, 5, 6, 7, 8, 128/DIG. 14, 348.1; 604/280, 283

[56] References Cited

U.S. PATENT DOCUMENTS

| | | | |
|---|---|---|---|
| 2,724,672 | 11/1955 | Rubin | 128/DIG. 14 X |
| 2,811,471 | 10/1957 | Homeyer . | |
| 2,814,583 | 11/1957 | Everett . | |
| 2,825,706 | 3/1958 | Sanders . | |
| 2,955,591 | 10/1960 | MacLean . | |
| 3,035,583 | 5/1962 | Hirsch et al. . | |
| 3,231,460 | 1/1966 | Andrews . | |
| 3,398,738 | 8/1968 | Lamb et al. . | |
| 3,618,614 | 11/1971 | Flynn | 604/282 X |
| 3,669,095 | 6/1972 | Kobayashi et al. . | |
| 3,960,143 | 6/1976 | Terada | 128/4 |
| 4,082,893 | 4/1978 | Okita . | |
| 4,208,745 | 6/1980 | Okita . | |
| 4,279,245 | 7/1981 | Takagi et al. | 128/4 |
| 4,332,242 | 6/1982 | Chikama | 128/3 |
| 4,336,794 | 6/1982 | Chikama | 128/4 |
| 4,413,359 | 11/1983 | Akiyama et al. . | |
| 4,536,179 | 8/1985 | Anderson et al. . | |
| 4,573,480 | 3/1986 | Hirschberg . | |
| 4,685,447 | 8/1987 | Iversen et al. . | |
| 4,713,070 | 12/1987 | Mano . | |

Primary Examiner—William H. Grieb
Attorney, Agent, or Firm—Wall and Roehrig

[57] ABSTRACT

A biopsy channel for a borescope or endoscope is formed of a thin-wall elastomeric tubular sleeve or sheath that is interference fitted over an expanded polytetrafluoroethylene (Teflon) liner. An end fitting can be formed of a metal or plastic tube, preferably with an internal chamfer. This can be secured by epoxy in either end of the channel, after suitably priming the elastomeric sleeve or sheath. This channel has high dimensional stability and can withstand bending to tight radii without kinking.

7 Claims, 1 Drawing Sheet

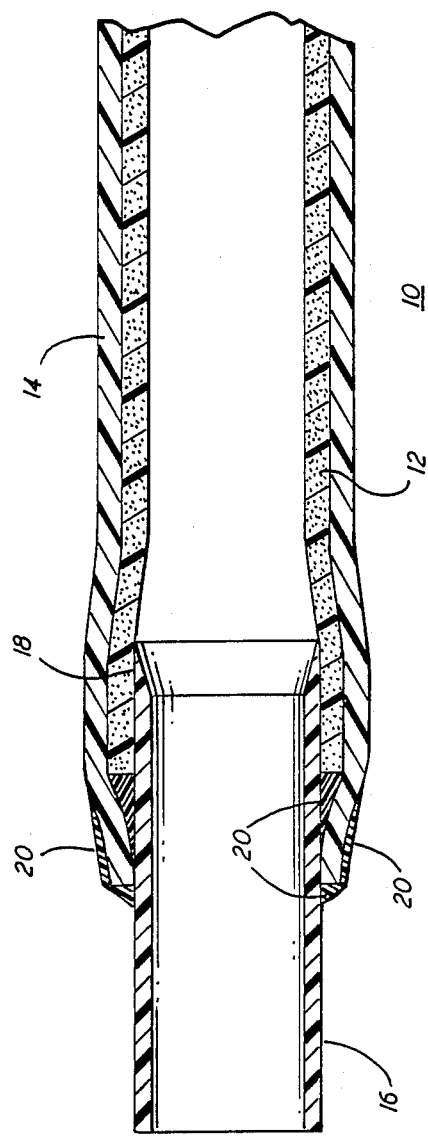

ELASTOMER-EPTFE BIOPSY CHANNEL

BACKGROUND OF THE INVENTION

The present invention relates to flexible tubes which can be favorably employed as a forceps channel or biopsy channel in an endoscope or a tool channel in a borescope. The invention is more particularly directed to flexible tubes which can be bent in rather tight circles without kinking, and which are gas- and liquid-tight.

Medical endoscopes, such as colonoscopes and gastroscopes, have elongated, flexible insertion tubes which can be inserted into a patient for observation and treatment of diseased tissues within e.g. the stomach or intestine. A biopsy channel or forceps channel extends within the endoscope insertion tube to permit an elongated medical instrument to be inserted through the endoscope into the viewing area thereof for removal or cauterization of tissue.

The path of the endoscope into the body is often rather tortuous, so the biopsy channel should be constructed to be highly flexible. Moreover, the channel must retain its open cross section and not kink when the channel flexes. The channel must also be impervious to fluids, so that fluids from the body tissues do not contact the insertion tube except at its outer sheath and inner surface of the channel. The channel and sheath should be sterilizable by flushing with guteraldehyde or the like.

One flexible tube for use as an endoscopic forceps channel is described in U.S. Pat. No. 4,279,245. In that case the tube is formed of a tubular crystalline fluoropolymer resin, such as PTFE to which is added a synthetic resin filler to make the tube gas-tight and water-tight. The filler resin enters the pores and interstices between PTFE fibrils from the outside of the tube and seals these gaps to a controlled depth. This tube is rather difficult to construct and, because the gaps among the PTFE fibrils are not open, but filled at and near the exterior surface, the tube is not as flexible as desirable.

OBJECTS AND SUMMARY OF THE INVENTION

It is an object of this invention to provide a biopsy channel or instrument-passage channel which overcomes the drawbacks of the prior art.

It is a more specific object of this invention to provide a biopsy or instrument-passage channel with low bending stiffness; ability to withstand bending cycles to a small bending radius without kinking; and ability to withstand pressures from about 40 psi of overpressure down to 12 psi of vacuum.

It is a further object of this invention to provide the channel with low internal friction and good conformability to pass medical (or industrial) instruments when the channel is bent to a small radius.

It is a still further object of this invention for the channel to be resistant to fluids such as alcohol, guteraldehyde, gasoline, hydraulic fluids, or other widely used medical or industrial liquids.

It is a yet-further object of this invention for the tubular channel to have good dimensional stability, especially in torsion.

It is another object of this invention to provide a channel in which end fittings can be easily and securely attached, e.g., with epoxy.

It is still another object of this invention for such end fittings to have minimal, if any, effect on the passage of instruments through the channel.

It is a still further object of this invention to provide the channel as a thin-wall tube of suitably small total diameter, so its presence has minimal effect on conductors, optical fibers, or other passages or tubes within the endoscope insertion tube.

It is a yet further object of the invention to provide a tubular channel which can be readily and quickly cleaned and disinfected after use.

In accordance with an aspect of the invention, a tubular instrument channel is formed of an inner liner of porous Teflon or ePTFE (expanded polytetrafluoroethylene) and an elastomeric outer sleeve. The outer sleeve has a free (or pre-assembly) inner diameter slightly smaller than the outer diameter of the inner liner. The sleeve can be of a very flexible elastomer such as silicone elastomer. End fittings of plastic or metal can be attached with epoxy. Most preferably these fittings are tubular with a chamferred inner surface to avoid an abrupt diameter change.

The tubular channels can be used in a wide variety of endoscopes (for medical or veterinary use) and borescopes (for industrial use), of either the video type or the fiber optic imaging type.

The above and other objects, features, and advantages of this invention will be more fully understood from the ensuing description of a preferred embodiment, when considered in connection with the accompanying Drawing.

BRIEF DESCRIPTION OF THE DRAWING

The sole Drawing Figure is a sectional view of a biopsy tube or channel according to a preferred embodiment of this invention.

DETAILED DESCRIPTION OF THE PREFERRED EMBODIMENTS

With reference to the sole Drawing Figure, an elastomeric/Teflon (ET) tubular biopsy passage 10 is formed of a porous ePTFE (expanded polytetrafluoroethylene) tubular liner 12 and a tubular elastomeric outer sleeve 14. In this case the liner 12 has an inner diameter of substantially 3.0 mm and a wall thickness of 0.4 mm, so the outer diameter is about 3.8 mm. The outer sleeve 14 has a slightly smaller inner diameter than the 3.8 mm outer diameter of the porous liner 12, prior to assembly. In this embodiment the sleeve walls are quite thin, nominally 0.25 mm. The wall thickness of the outer sleeve should be one-half millimeter or below. The sleeve 14 is interference-fitted onto the liner 12. To construct the biopsy passage 10, the elastomeric sleeve 14 is inflated slightly to stretch it to an increased diameter, and the liner 12 is inserted into the inflated sheath. Then the sheath 14 is permitted to relax into engagement with the liner 12. The combined tubular passage 10 should have a total (outer) diameter of four millimeters or less for an inner diameter of 3.0 millimeters.

A tubular end fitting 16 is inserted into the sleeve 14 and liner 12. One end of the fitting 16 inside the liner 12 has an internal chamfer 18. This avoids an abrupt diameter change within the passage 10 that might interfere with the travel of the elongated instrument through the passage. The fitting 16 can be stainless steel, nylon, vinyl, or another suitable plastic material, and is preferably secured by epoxy to the liner 12 and sleeve 14. The sleeve can be primed for this with a suitable treatment, such as isopropyl alcohol, although many other pretreatment components are available.

The sleeve 14 can be formed of any of a number of suitable materials, such as neoprene, fluoroelastomer, etc., and one silicone elastomer, namely Raychem SFR has performed well.

Sample passages 10 as described have been fabricated, with end fittings, and have been fitted into endoscopes. The biopsy passages 10 were tested and found to be excellent in terms of consistent inner diameter, bending stiffness, fatigue, forceps passage, medical material compatibility, external epoxy adhesion, internal abrasion, and internal pressurization capability.

One sample tubular passage 10 was installed into a 9.5 mm gastroscope. This gastroscope permitted passage of a colonoscope biopsy forceps tool under conditions of 210 degrees steering deflection, with 1½ loops in the insertion tube. The passage 10 operated satisfactorily under overpressures up to at least 40 psig and at vacuum down to about $-12$ psi.

These tubular passages can be constructed in a number of sizes, e.g., with inner diameters of 3.0, 3.2, or 3.8 mm. Inner diameters below 3.0 mm are possible.

While this invention has been illustrated and described with reference to a preferred embodiment, it should be understood that that embodiment serves as an example, and that many modifications and variations would present themselves to those of skill in the art without departure from the scope and spirit of this invention, as defined in the appended claims.

What is claimed is:

1. A flexible channel which is liquid impervious comprising
    a tubular inner liner of a flexible expanded polytetrafluoroethylene, having a predetermined inside diameter and outside diameter; and
    a tubular outer sleeve of an elastomer, having a free inside diameter smaller than the outside diameter of the inner tube, and stretch fit over said inner liner.
2. The flexible channel of claim 1 wherein said outer sleeve has a wall thickness when relaxed, of one half millimeter or below.
3. The flexible channel of claim 1 wherein said channel has a total diameter of not more than about 4 millimeters.
4. The flexible channel of claim 1 wherein said polytetrafluoroethylene inner tube has an inside diameter of 3.0 millimeters and a wall thickness of 0.4 millimeters.
5. The flexible channel of claim 4 wherein said elastomer outer sleeve has a wall thickness of 0.25 millimeters.
6. The flexible channel of claim 1 further comprising a rigid tubular fitting secured within one end of said channel.
7. The flexible channel of claim 6 wherein said tubular fitting has an internal chamfer at one end thereof which extends into said channel.

* * * * *